United States Patent
Marunaka et al.

(10) Patent No.: US 9,149,437 B2
(45) Date of Patent: Oct. 6, 2015

(54) METHOD FOR TREATMENT OF SOLID PHARMACEUTICAL PREPARATION PRIOR TO PRINTING AND SOLID PHARMACEUTICAL PREPARATION SUBJECTED TO TREATMENT PRIOR TO PRINTING

(75) Inventors: Shigeyuki Marunaka, Osaka (JP); Hikaru Fukuyama, Osaka (JP); Hiroshi Fukada, Osaka (JP); Toshihide Saito, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/659,630

(22) Filed: Mar. 15, 2010

(65) Prior Publication Data

US 2011/0014130 A1 Jan. 20, 2011

Related U.S. Application Data

(63) Continuation of application No. 10/581,071, filed as application No. PCT/JP2004/018112 on Nov. 30, 2004, now abandoned.

(30) Foreign Application Priority Data

Dec. 1, 2003 (JP) ................. 2003-401691

(51) Int. Cl.
| | |
|---|---|
| *A61K 9/44* | (2006.01) |
| *A61K 9/00* | (2006.01) |
| *A61K 9/30* | (2006.01) |
| *A61K 9/28* | (2006.01) |
| *A61J 3/00* | (2006.01) |
| *A61K 9/20* | (2006.01) |
| *B41M 3/00* | (2006.01) |
| *B41M 5/00* | (2006.01) |

(52) U.S. Cl.
CPC .............. *A61K 9/282* (2013.01); *A61J 3/007* (2013.01); *A61K 9/2072* (2013.01); *B41M 3/00* (2013.01); *B41M 5/0011* (2013.01)

(58) Field of Classification Search
CPC ....... A61J 3/007; A61K 9/2072; A61K 9/282; B41M 5/0011; B41M 3/00
See application file for complete search history.

(56) References Cited

U.S. PATENT DOCUMENTS

| | | | | |
|---|---|---|---|---|
| 3,751,277 A | * | 8/1973 | Small et al. | 106/162.1 |
| 4,456,629 A | | 6/1984 | Wood et al. | |
| 4,482,387 A | | 11/1984 | Wood et al. | |
| 5,314,697 A | * | 5/1994 | Kwan et al. | 424/480 |
| 6,117,479 A | | 9/2000 | Hogan et al. | |
| 6,254,888 B1 | | 7/2001 | Cappola | |
| 6,406,738 B1 | | 6/2002 | Hogan et al. | |
| 2001/0046517 A1 | * | 11/2001 | Kokubo et al. | 424/480 |

FOREIGN PATENT DOCUMENTS

| | | |
|---|---|---|
| CA | 1 222 696 A | 6/1987 |
| CA | 2 220 506 A1 | 11/1996 |
| JP | 53 052618 A | 5/1978 |
| JP | 54-138118 A | 10/1979 |
| JP | 54138118 A * | 10/1979 |
| JP | 11-507292 A | 6/1999 |
| WO | WO 92/13527 A1 | 8/1992 |
| WO | WO 94/02147 A1 | 2/1994 |
| WO | WO 96/35516 A1 | 11/1996 |
| WO | WO 00/57838 A2 | 10/2000 |

OTHER PUBLICATIONS

Uchiyama, Nobuo et al. English Machine Transaltion of the Abstract of JP-A-54-138118, published: Nov. 26, 1979.*
Office Action issued Mar. 14, 2011, in corresponding Canadian Application No. 2,547,495, 3 pages.
Porter et al., "Pan Coating of Tablets and Granules," Pharmaceutical Dosage forms: Tablets, vol. 3, p. 92-93, 1982.
Rangaiah et al., "Effects of Solvents, Temperature, and Plasticizer on Film Coating of Tablets," Drug Development and Industrial Pharmacy, 1997, vol. 23, No. 4, pp. 419-423.
Supplementary European Search Report, dated Jun. 24, 2011, EP 04 79 9960.
English translation of JP 53 052618, May 13, 1978 (cited in Aug. 12, 2011 IDS), 6 pages.

* cited by examiner

*Primary Examiner* — Johann R Richter
*Assistant Examiner* — Genevieve S Alley
(74) *Attorney, Agent, or Firm* — Foley & Lardner LLP

(57) ABSTRACT

The present invention provides a method for treating a solid dosage form to improve the printability and abrasion resistance of a print to be produced on a surface of the solid dosage form, which includes treating the surface of the solid dosage form with a polyethylene glycol-containing aqueous solution before printing; a production method of a solid dosage form with a printed surface, which includes printing on the surface after the aforementioned treatment; and a solid dosage form having a print improved in abrasion resistance on its surface, which can be obtained by the aforementioned production method.

9 Claims, No Drawings

METHOD FOR TREATMENT OF SOLID PHARMACEUTICAL PREPARATION PRIOR TO PRINTING AND SOLID PHARMACEUTICAL PREPARATION SUBJECTED TO TREATMENT PRIOR TO PRINTING

CROSS-REFERENCE TO RELATED APPLICATIONS

This application is a Continuation of U.S. application Ser. No. 10/581,071, which is the U.S. National Stage application of PCT/JP2004/018112, filed Nov. 30, 2004, which claims priority from patent application No. 2003-401691 filed in Japan on Dec. 1, 2003, the contents of each of the aforementioned applications are incorporated in full herein by this reference.

TECHNICAL FIELD

The present invention relates to a method for treating a solid dosage form to improve the printability and abrasion resistance of a print to be produced on a surface of the solid dosage form, and a solid dosage form having improved abrasion resistance of a print or improved printability, which is afforded by the treatment.

BACKGROUND ART

There are many kinds of tablets and capsules that resemble one another in the size, color tone and shape. To identify each preparation, a company name, a company mark, a product name, active ingredient contents and the like are often coded and directly imprinted on the preparation. For imprinting, engraving and printing are available. While engraving is employed for plain tablets free of coating, a subset of film-coated tablets and the like, printing is employed for many film-coated tablets, sugar-coated tablets, capsules and the like.

For tablets and capsules, polishing with wax (in this specification, it means "wax" in a narrow sense, namely, fatty acid ester of higher alcohol: examples: carnauba wax, bees wax and the like) is often applied for the purpose of increasing the commercial value by glossy appearance, protecting a preparation from highly humid environment, preventing staining with coloring agents, improving slip property to facilitate handling in later operations of printing, inspection, packing and the like, and the like (e.g., Porter and two others, Pan Coating of Tablets and Granules, edited by Herbert A. Lieberman and one other, *Pharmaceutical Dosage Forms Tablets*, vol. 3, US, Marcel Dekker Inc., 1982, p. 92). Wax can be used by dissolving in an organic solvent such as chloroform/acetone and the like, or suspending in a dispersion medium such as alcohol and the like, or directly applied to the surface of a preparation as a fine powder. However, it is desirable to avoid use of an organic solvent in view of the safety issue caused by a residual solvent, a large scale facility required to prevent accident and environmental pollution, and the like. Moreover, the use of a suspension and a powder may cause non-uniform coating, possibly leading to inconvenience.

Furthermore, polishing with a wax prior to printing may cause easy scratch of prints and stain of the preparation itself as well as containers, which in turn impairs identification function and also reduces the commercial value due to the defective appearance. In addition, some kind of wax provides too much polish that can cause printing failure, and decrease the product yield (e.g., U.S. Pat. No. 4,456,629 (column 1, lines 34-39)).

DISCLOSURE OF THE INVENTION

It is therefore an object of the present invention to provide a method of polishing a solid dosage form without using an organic solvent, which can improve and abrasion resistance of a print and printability of the solid dosage form, and a solid dosage form improved in the abrasion resistance of a print and/or printability based on the method.

The present inventors have conducted intensive studies in an attempt to solve the aforementioned problem and surprisingly found that the printability during printing and abrasion resistance of the print after printing of a solid dosage form can be remarkably improved, as compared to conventional tablets polished with a wax, by treating a surface thereof with a polyethylene glycol-containing aqueous solution prior to printing. The present inventors have conducted further studies based on these findings and completed the present invention.

Accordingly, the present invention provides

[1] a treatment method for improving printability and/or abrasion resistance of a print to be produced on a surface of a solid dosage form, which comprises treating said surface with a polyethylene glycol-containing aqueous solution before printing,

[2] the method of the above-mentioned [1], wherein polyethylene glycol has an average molecular weight of not less than about 1,000,

[3] the method of the above-mentioned [1], wherein polyethylene glycol has an average molecular weight of about 3,000 to about 9,000,

[4] the method of the above-mentioned [1], wherein the amount of polyethylene glycol to be added by the treatment is about 0.01% to about 1.0% in a weight ratio to the finished preparation,

[5] the method of the above-mentioned [1], wherein the solid dosage form is a film-coated tablet,

[6] a method for producing a solid dosage form with a printed surface, which comprises treating the surface of the solid dosage form with a polyethylene glycol-containing aqueous solution and then printing on said surface,

[7] the method of the above-mentioned [6], wherein polyethylene glycol has an average molecular weight of not less than about 1,000,

[8] the method of the above-mentioned [6], wherein polyethylene glycol has an average molecular weight of about 3,000 to about 9,000,

[9] the method of the above-mentioned [6], wherein the amount of polyethylene glycol to be added by the treatment is about 0.01% to about 1.0% in a weight ratio to the finished preparation,

[10] the method of the above-mentioned [6], wherein the solid dosage form is a film-coated tablet,

[11] a solid dosage form treated by the method of any of the above-mentioned [1] to [5],

[12] a solid dosage form with a printed surface, which can be obtained by any of the above-mentioned [6] to [10],

[13] a solid dosage form which has a coating film comprising polyethylene glycol but free of bees wax and carnauba wax on its surface, and is printed on the surface of the coating film, and

[14] a solid dosage form which has a coating comprising polyethylene glycol but free of bees wax and carnauba wax on its surface, and is printed on the surface of the coating.

DETAILED DESCRIPTION OF THE INVENTION

The present invention provides a method for treating a solid dosage form to improve the abrasion resistance of a print to be produced on a surface of the solid dosage form. As used herein, by "to improve the abrasion resistance of a print" is meant, for example, significantly reducing the degree of abrasion of the print produced on the solid dosage form as compared to a case free of such treatment, in the print abrasion test to be described in detail in the Examples to be mentioned below.

The solid dosage form applicable to the treatment method of the present invention is not particularly limited in the dosage form as long as its surface can be printed on and, for example, tablet, capsule, troche pill, suppository and the like can be mentioned. In view of the necessity of imprinting by printing, the method is particularly preferably applied to tablets and capsules.

In this specification, the "solid dosage form" means not only pharmaceutical products but also any composition processed to have a certain dosage form of animal drug, agricultural chemical, fertilizer, sanitary products and the like.

The active ingredient to be contained in the solid dosage form is not particularly limited. For example, substances effective for the prophylaxis or treatment of various diseases, which are exemplified by, but not limited to, substances having sleep-inducing action, tranquilizer activity, antibiotic activity, hypotensive action, antianginal activity, analgesic activity, anti-inflammatory activity, mental stabilizing action, diabetes treatment activity, diuretic action, anticholine activity, antihyperacidic action, antiepileptic action, ACE inhibitory activity, β-receptor antagonistic or agonistic activity, anesthetic action, anorexigenic action, antiarrhythmic action, antidepressive action, anticoagulant activity, anti diarrheal action, antihistaminic activity, antimalarial action, antitumor activity, immunosuppressive activity, anti-Parkinson's syndrome action, antipsychotic action, antiplatelet activity, antihyperlipidemic action and the like, and the like, substance having detergent action, substances having flavoring, fertilizer, and deodorizing actions, animal/pest exterminating substances, substances having insecticidal action, substances having herbicidal action, plant growth regulators and the like.

Where necessary, the solid dosage form of the present invention can contain a carrier acceptable for the use of the solid dosage form, together with the active ingredient. In the case of a pharmaceutical preparation, for example, it can contain a pharmaceutically acceptable carrier. As the pharmaceutically acceptable carrier, various organic or inorganic carriers conventionally used as preparation materials are used and, for example, excipient, lubricant, binder, disintegrant, thickener and the like are appropriately added in suitable amounts. Where necessary, additives such as preservative, antioxidant, coloring agent, sweetening agent and the like can also be used.

Examples of the excipient include, but are not limited to, lactose, sucrose, glucose, maltose, corn starch, flour starch, mannitol, xylitol, sorbitol, maltitol, erythritol, lactitol, palatinit, crystalline cellulose, light anhydrous silicic acid, dextrin, carboxymethylstarch, gelatin, synthesis aluminum silicate, magnesium alumino metesilicate, magnesium oxide, calcium phosphate, calcium carbonate, calcium sulfate and the like.

Examples of the lubricant include, but are not limited to, stearic acid, magnesium stearate, calcium stearate, talc, waxes, DL-leucine, sodium lauryl sulfate, magnesium lauryl sulfate, polyethylene glycol, light anhydrous silicic acid (usable as antistatic agent) and the like.

Examples of the binder include, but are not limited to, gelatin, pullulan, hydroxypropylmethylcellulose (HPMC), hydroxypropylcellulose (HPC), methylcellulose (MC), crystalline cellulose, polyvinylpyrrolidone (PVP), polyethylene glycol, gum arabic, dextran, polyvinyl alcohol (PVA), starch paste and the like.

Examples of the disintegrant include, but are not limited to, carboxymethylcellulose, calcium carboxymethylcellulose, low-substituted hydroxypropylcellulose, crosslinking polyvinylpyrrolidone, carmellose sodium, croscarmellose sodium, sodium carboxymethyl starch, cation exchange resin, partially pregelatinized starch, corn starch and the like.

Examples of the thickener include, but are not limited to, natural rubbers, cellulose derivative, acrylic acid polymer and the like.

Examples of the preservative include, but are not limited to, p-hydroxybenzoic acid esters, chlorobutanol, benzyl alcohol, phenethyl alcohol, dehydroacetic acid, sorbic acid and the like.

Examples of the antioxidant include, but are not limited to, sulfite, ascorbic acid and their alkali metal salts, alkaline earth metal salts and the like.

Examples of the coloring agent include, but are not limited to, synthetic coloring agents applicable to pharmaceutical products (e.g., sunset yellow etc. and aluminum lake thereof and the like), yellow ferric oxide, red ferric oxide, riboflavin, riboflavin organic acid esters (e.g., riboflavin butyric acid ester), phosphoric acid riboflavin or alkali metal salt thereof, alkaline earth metal salt, phenol phthalein, titanium oxide and the like. As the light shielding agent, titanium oxide and the like can be mentioned.

Examples of the sweetening agent include, but are not limited to, saccharin sodium, dipotassium glycyrrhizinate, aspartame, stevia and the like.

The solid dosage form of the present invention can be formulated into a dosage form suitable for oral administration, which is exemplified by, but not limited to, tablet, capsule and the like or parenteral administration such as suppository and the like, by processing the above-mentioned active ingredient and a suitable carrier according to a method known per se.

Tablets can be coated by a method known per se for the purpose of making a smell or taste, stabilizing components, maintaining efficacy and the like. The coating can be largely divided into sugar coating and film coating (including enteric coating and the like) according to its kind.

As a coating agent for sugar coating, sucrose is generally used. To enhance the binding property of a sugar coating layer and increase the mechanical strength, gelatin, gum arabic, methylcellulose, carboxymethylcellulose, sodium carboxymethylcellulose, sodium starchglycolate, crystalline cellulose, polyvinylpyrrolidone, polyvinyl alcohol, sodium alginate and the like can be added. Furthermore, as an excipient or anti-tack agent, talc, precipitated calcium carbonate, kaolin and the like are used, and, for masking or shading of color, a masking agent such as titanium oxide and the like are used.

As the film coating agent, for example, hydroxypropylmethylcellulose, ethylcellulose, hydroxypropylcellulose, tween80, and dyes such as titanium oxide, ferric oxide (e.g., red ferric oxide, yellow ferric oxide) and the like are used.

Moreover, photostability and the like can be improved by adding a masking agent and the like. These film coating formulations may contain, where necessary, talc and other excipients applicable to pharmaceutical products. As the film coating agent, a base agent aiming at enteric coating and controlled release may be used besides those used for masking a taste, enhancing photostability or improving appearance. As a base agent for the film coating, hydroxypropylcellulose (HPC), hydroxypropylmethylcellulose (HPMC), polyvinylpyrrolidone (PVP), ethylcellulose, polyvinyl acetal diethylamino acetate, cellulose acetate phthalate, methacrylic acid copolymers (e.g., methyl methacrylate-methacryl acid copolymers (Eudragit L100 or S100, manufactured by Rohm), methacrylic acid-ethyl acrylate copolymers (Eudragit L100-55, L30D-55), methacrylic acid-methyl acrylate-methyl methacrylate copolymers (Eudragit FS30D, manufactured by Rohm)), hydroxypropylmethylcellulose phthalate (HP-55, HP-50, manufactured by Shin-Etsu Chemical Co., Ltd.), carboxymethylethylcellulose (CMEC, manufactured by Freund Corporation), hydroxypropylmethylcellulose acetate succinate (HPMCAS, manufactured by Shin-Etsu Chemical Co., Ltd.), polyvinyl acetate phthalate, shellac and the like can be used. They may be used alone, or at least two or more kinds of polymers may be applied in combination, or at least two or more kinds of polymers may be applied successively.

Of these, as a coating material for controlling the release of the active ingredient in a pH-dependent manner, hydroxypropylmethylcellulose phthalates (HP-55, HP-50, manufactured by Shin-Etsu Chemical Co., Ltd.), cellulose acetate phthalate, carboxymethylethylcellulose (CMEC, manufactured by Freund Corporation), methyl methacrylate-methacrylic acid copolymers (Eudragit L100 or S100, manufactured by Rohm), methacrylic acid-ethyl acrylate copolymers (Eudragit L100-55, L30D-55), methacrylic acid-methyl acrylate-methyl methacrylate copolymer (Eudragit FS30D, manufactured by Rohm), hydroxypropylmethylcellulose acetate succinate (HPMCAS, manufactured by Shin-Etsu Chemical Co., Ltd.), polyvinyl acetate phthalate, shellac and the like can be used.

The coating agents may be used alone or in combination as necessary. Where necessary, plasticizer, stabilizer and the like such as polyethylene glycol, dibutyl sebacate, diethyl phthalate, triacetine, triethyl citrate, copolyvidon and the like may be used for coating.

For coating, a method known per se, such as a pan coating method using a perforated coating system (e.g., Hicoater (trademark); Freund Corporation) and the like using a coating pan, a fluid bed coating method using a fluid bed granulation coating system (e.g., flow coater (trademark); Freund Corporation) and the like, is employed.

Capsules can be produced by packing the above-mentioned active ingredient powder, or a powder mixture of the active ingredient and the above-mentioned carrier, or fine granules or granules obtained by kneading or granulating the powder mixture and the like in a suitable capsule. The packed material (particularly fine particles or granules) may be film-coated as necessary, in a similar manner as that mentioned above with regard to the tablet.

As the capsule, one containing polyhydric alcohol such as glycerol, propylene glycol and the like or saccharide such as mannitol, sorbit and the like as a plasticizer in gelatin, which is molded suitably can be mentioned. Where necessary, the capsule may further contain a coloring agent and a preservative similar to those mentioned above.

The treatment method of the present invention may be applied to a capsule filled with the packing material such as an active ingredient and the like. Alternatively, an empty capsule may be subjected to the treatment method of the present invention, printed and filled with a packing material to give a finished preparation.

The treatment method of the present invention can also be applied not only to the above-mentioned solid dosage form but also any solid composition desired to carry a print on its surface such as a food (e.g., sugar coated chocolate, gum, supplement and the like) and the like, particularly a solid composition requiring or desirably subjected to a treatment for improving the slip property and gloss.

The treatment method of the present invention is characterized by a treatment of a surface of the solid dosage form with a polyethylene glycol-containing aqueous solution before printing. As used herein, by the "treatment" is meant "to apply" and refers to bringing a polyethylene glycol-containing aqueous solution into contact with the surface of a solid dosage form after treatment, such that polyethylene glycol remains on the surface.

Polyethylene glycol to be used in the present invention is not particularly limited as long as it is not subject to any limitation due to other reasons (e.g., range acceptable as a pharmaceutical additive when the solid dosage form is a pharmaceutical preparation). In consideration of the object of the present invention to improve durability of a print, however, polyethylene glycol is desirably present as a solid at a temperature of the environment (e.g., 0 to 40° C., 10 to 30° C., 15 to 25° C.) where the solid dosage form is preserved. For example, one having an average molecular weight of about not less than 1,000, more preferably about 3,000 to about 9,000, can be mentioned. In addition, two or more kinds of polyethylene glycol having different average molecular weights may be used in a mixture.

The average molecular weight of polyethylene glycol is measured by a method according to the measurement method of the average molecular weight of macrogol 4000 in the Japan Pharmacopoeia fourteenth Edition (hereinafter sometimes to be abbreviated simply as the Japan Pharmacopoeia).

The concentration of polyethylene glycol in the polyethylene glycol-containing aqueous solution is not particularly limited as long as it ensures that polyethylene glycol remains on the surface of a solid dosage form after treatment in an amount sufficient to improve the abrasion resistance of a print to be produced on said surface. For example, it is about 1 to about 20 wt %, preferably about 5 to about 15 wt %.

The polyethylene glycol-containing aqueous solution can contain a component other than polyethylene glycol within the range free of a bad influence on the property of a print to be produced on the surface of a solid dosage form. As used herein, by the "property of a print" is meant properties including quantitative and qualitative characteristics during printing, such as abrasion resistance after printing, incidence of incomplete print, printing stain and the like (=rate of printing failure) and level of the printing failure. For example, when the treatment method of the present invention is applied to a plain tablet, the polyethylene glycol-containing aqueous solution contains a film coating agent since the solution also functions as a film coating liquid, as mentioned above. As the film coating agent, for example, those capable of being dispersed in a water-soluble or aqueous solution can be mentioned, from the above-mentioned film coating agents.

In addition, the polyethylene glycol-containing aqueous solution can further contain a preparation additive as necessary, such as stabilizer, lubricant, preservative, antioxidant, coloring agent, sweetening agent and the like. As the stabilizer, for example, tartaric acid, citric acid, succinic acid, fumaric acid, maleic acid and the like can be mentioned. As the lubricant, for example, talc, titanium oxide, magnesium stearate, calcium stearate, light anhydrous silicic acid and the like can be mentioned. As the preservative, for example, p-hydroxybenzoic acid esters, chlorobutanol, benzyl alcohol, phenethyl alcohol, dehydroacetic acid, sorbic acid and the like can be mentioned. As the antioxidant, for example, sulfite, ascorbate and the like can be mentioned. As the coloring agent, for example, water-soluble food tar colors (e.g., food dyes such as Food Red No. 2 and No. 3, Food Yellow No. 4 and No. 5, Food Blue No. 1 and No. 2 and the like), water insoluble lake colors (e.g., aluminum salts of the aforementioned water-soluble food tar colors), natural colors (e.g., β-carotene, chlorophyll, ferric oxide) and the like can be mentioned. As the sweetening agent, for example, sodium saccharin, dipotassium glycyrrhizinate, aspartame, stevia and the like can be mentioned.

As mentioned above, the film coating liquid can contain a plasticizer to control the softening temperature of the coating agent. When the polyethylene glycol-containing aqueous solution is a film coating liquid, polyethylene glycol itself can function as a plasticizer. A polyethylene glycol-containing aqueous solution having a concentration necessary for improving the abrasion resistance of a print to be produced on the surface of a solid dosage form is sufficient to function as a plasticizer. When desired, other plasticizers, such as acetyltributyl citrate, acetyltriethyl citrate, castor oil, diacetylation monoglyceride, dibutyl sebacate, diethyl phthalate, glycerol, mono- or di-acetylation monoglyceride, propyleneglycol, triacetine, triethyl citrate and the like may be further added.

When the polyethylene glycol-containing aqueous solution contains a component other than polyethylene glycol, the proportion of polyethylene glycol in the whole components (excluding water) is about 1 to about 30 wt %, preferably about 10 to about 20 wt %.

For a treatment of the surface of a solid dosage form with a polyethylene glycol-containing aqueous solution, various coating methods generally used in the field of preparations can be employed. Preferably, spray coating is applied using a coating pan, a fluid bed coating system and the like.

In the case of sugar-coated tablets, for example, after completion of each step of sugar coating (i.e., waterproof coating, under coating, sub-coating, coloring, finishing), tablets are transferred to a cloth polishing pan, a predetermined amount of a polyethylene glycol-containing aqueous solution is sprayed or poured thereon while rotating the pan, or a polyethylene glycol-containing aqueous solution is sprayed or poured thereon once to several times while rotating the pan until it reaches a predetermined coating weight.

In the case of film-coated tablets, for example, a polyethylene glycol-containing aqueous solution is sprayed with a compressed air from a spray nozzle in the coating pan used for the film coating while rotating the pan, and the surface of the tablets is dried by heated air supplied. Alternatively, in the fluid bed coating system used for the film coating, a polyethylene glycol-containing aqueous solution is sprayed from a spray nozzle while floating or fluidizing the tablets with an air flow and the surface of the tablets is dried with the air flow. The polyethylene glycol-containing aqueous solution is sprayed in a predetermined amount, or the above-mentioned operation is repeated until a predetermined coat weight is achieved.

In the case of plain tablets, namely, when a polyethylene glycol-containing aqueous solution also functions as a film coating liquid, a method employed for conventional film coating can be used directly. For example, a method similar to that of the above-mentioned film-coated tablets can be mentioned.

In the case of capsule, too, a method employed for conventional film coating can be used similarly. When this treatment is applied after filling packing materials such as an active ingredient and the like, powder of the packing materials attached to the surface of the capsule during the filling is preferably removed with a conventional capsule polishing machine before the treatment.

The weight of the coating film formed by the treatment method of the present invention is not particularly limited as long as it ensures that polyethylene glycol remains on the surface of a solid dosage form after treatment in an amount sufficient to improve the abrasion resistance of a print to be produced on said surface. Preferably, it is appropriately selected from the range that makes the weight ratio of the amount of polyethylene glycol to be added by this treatment to the finished preparation fall within the range of about 0.01 to about 1.0%, more preferably about 0.05% to about 0.7%.

The treatment method of the present invention can not only improve the abrasion resistance of a print to be produced on the surface of a solid dosage form, but also reduce the frequency of printing failure (i.e., printing failure rate) during printing such as incomplete print, printing stain and the like, and advantageously further improve the printing performance as a whole.

Accordingly, the present invention also relates to a production method of a solid dosage form having a print on its surface, which comprises treating the surface of the solid dosage form with a polyethylene glycol-containing aqueous solution and then printing on said surface. The treatment with a polyethylene glycol-containing aqueous solution can be applied as mentioned above.

For printing, a method conventionally used in the art can be employed. As a solid dosage form delivery mechanism of a printing machine, any type can be used, including a slot type, a drum type, a link type and the like, and an appropriate type can be selected according to the manufacturing scale and the like. While the printing method is not particularly limited, either, a photogravure offset printing method is often used. To be specific, a photogravure roll engraved with an identification code, a symbol and the like during a photomechanical process is rotated in an ink tank to attach the ink, and redundant ink is scraped off with a blade (thin-bladed knife). The ink remaining in the engraving (concave) is transferred onto a rubber offset roll, and then transferred onto the solid dosage form in a printing section to complete the printing. As the tablet (capsule) printing machine, commercially available ones from Markem Corporation, Hartnett, Matsuoka Machinery Works Co., Ltd, Qualicaps Co., Ltd. and the like can be used.

While the ink to be used for printing is not particularly limited as long as it is harmless, it is desirably quick-drying, and has high abrasion resistance after drying. As the dye, titanium oxide, carbon black, iron oxide, tar dyes (e.g., acidic colors such as Red No. 2, Red No. 3, Red No. 102, Red No. 104-(1), Red No. 105-(1), Red No. 106, Yellow No. 4, Yellow No. 5, Green No. 5, Blue No. 1, Blue No. 2 and the like) and the like are generally used. As the base agent, moreover, shellac and the like are used and, as the solvent, ethanol, n-butanol, isopropanol and the like are used.

The solid dosage form with a print on its surface, which is produced by the above-mentioned method, has novel and useful characteristic in that it shows remarkably improved abrasion resistance of prints as compared to conventional preparations obtained by applying, before printing, a polishing treatment with a wax solution using an organic solvent or a powder wax or a wax-like substance. Accordingly, the present invention also provides a solid dosage form obtained by the above-mentioned method, which has a print on its surface.

The solid dosage form of the present invention can be conferred a desirable characteristic of superior abrasion resistance of a print produced on its surface, due to the presence of a coating film containing polyethylene glycol on the surface of the solid dosage form. The "coating film" does not need to completely cover the surface of a solid dosage form, as long as polyethylene glycol is substantially uniformly present at least on the area to be printed on. For example, the "coating film" may be in the state where a number of miniature films attach to the surface of a solid dosage form. As used herein, by "substantially uniform" is meant being uniform to a degree sufficient to improve the abrasion resistance of the print. Therefore, the solid dosage form of the present invention is not restricted to the above-mentioned method, as long as it has the above-mentioned surface structure and superior abrasion resistance of the print, and may be produced by any method.

Preferably, the solid dosage form of the present invention does not contain bees wax and carnauba wax in the coating film containing polyethylene glycol.

The solid dosage form of the present invention can be administered to the subject in the same manner as in conventional solid dosage forms.

The present invention is explained in detail in the following by referring to Examples, which are mere examples and do not limit the scope of the present invention in any way.

Example 1

Reference Example

Production of Film-Coated Tablet

| Formulation (unit: mg) | | |
|---|---|---|
| plain tablet (containing 4 mg of active ingredient) | 130.0 | |
| hydroxypropylmethylcellulose (TC-5; trademark) | 3.74 | (74.8%) |
| copolyvidon | 0.75 | (15.0%) |
| titanium oxide | 0.5 | (10.0%) |
| yellow ferric oxide | 0.01 | (0.2%) |
| total | 135.0 | |

Plain tablets were placed in a coating machine (Driacoater (Powrex Corporation) or Hicoater (Freund Corporation)), a film coating liquid containing TC-5, copolyvidon, titanium oxide and yellow ferric oxide at the above-mentioned weight ratios was sprayed with a spray nozzle while rotating the pan, and the tablets were dried by heated air supplied. This operation was repeated until the above-mentioned coating weight was achieved.

Example 2

Pre-Printing Treatment with Polyethylene Glycol-Containing Aqueous Solution

| formulation (unit: mg) | Prepar. Ex. 1 | Prepar. Ex. 2 | Comp. Ex. |
|---|---|---|---|
| film-coated tablet (Reference Example) | 135.0 | 135.0 | 135.0 |
| MACROGOL 4000 (the Japan Pharmacopoeia) | 0.1 | | |
| MACROGOL 6000 (the Japan Pharmacopoeia) | | 0.1 | |
| water | (0.9) | (0.9) | |
| carnauba wax | | | 0.008 |
| sorbitan mono-oleate | | | 0.04 |
| n-hexane | | | (0.9625) |

The film-coated tablets (6,000 tablets, 810 g) obtained in the above-mentioned Reference Example were placed in a Hicoater (Freund Corporation), and a 10 wt % aqueous solution of MACROGOL 4000 (the Japan Pharmacopoeia; molecular weight 2,600-3,800) (Preparation Example 1) or MACROGOL 6000 (the Japan Pharmacopoeia; molecular weight 7,300-9,300) (Preparation Example 2) in total 6.0 g, or a 0.79 wt % carnauba wax n-hexane solution (Comparative Example) in total 6.063 g was sprayed while rotating the pan to give respective tablets having the above-mentioned formulations.

The above-mentioned respective tablets were printed on by a conventional method using an organic solvent type ink (manufactured by Colorcon. Inc.) with a tablet printing machine (Matsuoka Machinery Works Co., Ltd).

Example 3

Experimental Example

Test of Print Abrasion Resistance of and Printing Failure Rate

The three kinds of tablets (500 tablets each) obtained in the above-mentioned Example 2 were visually observed to examine printing failure, and 100 tablets each were placed in glass bottles, which were shaken at amplitude 40 mm, shaking speed 250 times/minute in a reciprocal shaker SR-IIw (Nihon Medical and Chemical instruments Co., Ltd.) to observe the level of abrasion of the print over time. The results are shown in Table 1.

TABLE 1

| | | Comp. Ex. | Prep. Ex. 1 | Prep. Ex. 2 |
|---|---|---|---|---|
| appearance | number of test tablets | 500 | 500 | 500 |
| | Class D (%)[1] | 0 | 0 | 0 |
| | Class C (%) | 0 | 0 | 0 |
| | Class B (%) | 2.0 | 0 | 0 |
| | incomplete print | | | |
| | printing stain | 1.4 | 1.2 | 0.8 |
| | total | 3.4 | 1.2 | 0.8 |
| abrasion property[2] | 10 min | print is scratchy, whole tablet is stained (+) | no change (±) | no change (±) |
| | 30 min | print is scratchy, whole | print is scratchy, whole | no change (±) |

TABLE 1-continued

|  | Comp. Ex. | Prep. Ex. 1 | Prep. Ex. 2 |
|---|---|---|---|
| 60 min | tablet is stained (++) print is scratchy, whole tablet is stained (+++) | tablet is stained (+) print is scratchy, whole tablet is stained, cloudy bottle (++) | print is scratchy, whole tablet is stained, cloudy bottle (++) |

[1]Class of appearance Class B: readable print though partly missing, or printing stain of not more than 1 mm in length Class C: partly unreadable print, or printing stain of more than 1 mm in length Class D: unreadable print
[2]Abrasion property (±): No change from the start of shaking (+): readable print though with slight change in printing state (scratching, stain and the like) (++): clear change in printing state and partly unreadable print (+++): marked change in printing state and mostly unreadable print As is clear from Table 1, a pretreatment with a polyethylene glycol-containing aqueous solution resulted in remarkably improved abrasion resistance of the print as compared to the use of carnauba wax. Moreover, the printing failure rate showed a tendency toward lower levels. More superior results were obtained in both the abrasion resistance and printing failure rate by the use of MACROGOL 6000 The Japanese Pharmacopoeia.

INDUSTRIAL APPLICABILITY

According to the treatment method of the present invention, printability and abrasion resistance of a print to be produced on a surface of the solid dosage form can be improved, and as a result, identification function of the solid dosage form can be maintained for a long time and good appearance is not impaired, and a solid dosage form with a high commercial value can be provided.

The method for treating a solid dosage form of the present invention provides an effect of remarkably improved printability and abrasion resistance of the solid dosage form by treating, before printing, the surface of the solid dosage form with a polyethylene glycol-containing aqueous solution.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claims.

Those described in a singular form in the present specification may be understood in a plural form, as long as they are not associated with clear inconsistencies with the context and the present invention.

All references cited herein, including patents and patent applications, are hereby incorporated in full by reference, to the extent that they have been disclosed herein.

The invention claimed is:

1. A treatment method for improving printability or abrasion resistance of a print to be produced on a surface of a solid dosage form, which comprises treating said surface with an aqueous solution consisting of polyethylene glycol and water before printing, wherein said solid dosage form is a film-coated tablet, and the film coating comprises, as a base agent, one or more agents selected from the group consisting of hydroxypropylcellulose, hydroxypropylmethylcellulose, polyvinylpyrrolidone, ethylcellulose, polyvinyl acetal diethylamino acetate, cellulose acetate phthalate, methacrylic acid copolymers, hydroxypropylmethylcellulose phthalate, carboxymethylethylcellulose, hydroxypropylmethylcellulose acetate succinate, polyvinyl acetate phthalate and shellac.

2. The method of claim 1, wherein polyethylene glycol has an average molecular weight of not less than 1,000.

3. The method of claim 1, wherein polyethylene glycol has an average molecular weight of 3,000 to 9,000.

4. The method of claim 1, wherein the amount of polyethylene glycol to be added by the treatment is 0.01% to 1.0% in a weight ratio to the finished preparation.

5. A method for producing a solid dosage form with a printed surface, which comprises treating the surface of the solid dosage form with an aqueous solution consisting of polyethylene glycol and water and then printing on said surface, wherein the solid dosage form is a film-coated tablet and said polyethylene glycol has an average molecular weight of not less than 1,000.

6. The method of claim 5, wherein polyethylene glycol has an average molecular weight of 3,000 to 9,000.

7. The method of claim 5, wherein the amount of polyethylene glycol to be added by the treatment is 0.01% to 1.0% in a weight ratio to the finished preparation.

8. The method of claim 1, wherein the concentration of polyethylene glycol in the polyethylene glycol-containing aqueous solution is about 1 to about 20 wt %.

9. The method of claim 5, wherein the concentration of polyethylene glycol in the polyethylene glycol-containing aqueous solution is about 1 to about 20 wt %.

* * * * *